US005770206A

United States Patent [19]
Nicolicchia

[11] Patent Number: 5,770,206
[45] Date of Patent: Jun. 23, 1998

[54] BODY OILS AND METHOD FOR MAKING THE SAME

[75] Inventor: Carlo Nicolicchia, Egg Harbor, N.J.

[73] Assignee: C&D Master Enterprizes Ltd, Egg Harbor, N.J.

[21] Appl. No.: 770,002

[22] Filed: Dec. 19, 1996

[51] Int. Cl.$^6$ .......... A61K 35/78; A61K 39/385; A61K 47/00
[52] U.S. Cl. .......... 424/195.1; 514/783; 514/789
[58] Field of Search .......... 424/195.1; 514/783, 514/789

[56] References Cited

U.S. PATENT DOCUMENTS

| | | |
|---|---|---|
| 1,516,562 | 11/1924 | Calabro . |
| 2,898,269 | 8/1959 | Felletschin .................. 167/90 |
| 4,608,392 | 8/1986 | Jacquet et al. .................. 514/844 |
| 4,742,083 | 5/1988 | Ritchey .................. 514/617 |
| 4,911,925 | 3/1990 | Shatkina et al. .................. 424/401 |
| 4,931,271 | 6/1990 | Lang et al. .................. 424/47 |
| 4,986,986 | 1/1991 | Roth .................. 424/195.1 |
| 5,034,215 | 7/1991 | Roth .................. 424/61 |
| 5,063,062 | 11/1991 | Greenspan et al. .................. 424/443 |
| 5,106,622 | 4/1992 | Sherwood et al. .................. 424/195.1 |
| 5,182,105 | 1/1993 | Takata et al. .................. 424/78.02 |
| 5,223,257 | 6/1993 | Arora .................. 424/195.1 |
| 5,242,952 | 9/1993 | Tritsarolis .................. 514/783 |
| 5,322,689 | 6/1994 | Hughes et al. .................. 424/401 |
| 5,498,637 | 3/1996 | Timmermeyer et al. .................. 424/195.1 |

*Primary Examiner*—Kimberly Jordan
*Attorney, Agent, or Firm*—Breiner & Breiner

[57] ABSTRACT

Body oils of all natural ingredients are disclosed having a base oil, such as virgin olive oil, which serves as a carrier for flavoring(s) or fragrance(s), sensory material(s), and optionally a sweetener. Application of the oil provides sensory stimulation and is not harmful upon ingestion.

28 Claims, No Drawings

BODY OILS AND METHOD FOR MAKING THE SAME

FIELD OF THE INVENTION

The present invention relates to body oils containing all natural components, in particular natural flavors, sensory materials and base oil. The body oils of the invention are particularly useful as "erotic" body oils.

BACKGROUND OF THE INVENTION

Body oils and lotions are often used for skin moisturizing or to relieve pain in muscles. Many of these products, however, contain non-natural ingredients, such as fragrances, perfumes, extracts, preservatives, pest-repellants, sunscreens, etc. which are not only unpleasant if ingested but which also can be harmful. Further, few of these products contain sensory stimulants which some users may find particularly desirable.

The foregoing illustrates limitations known to exist in present body oils. Thus, it is apparent that it would be advantageous to provide an improved body oil directed to overcoming one or more of the limitations set forth above. Accordingly, a suitable alternative is provided including features more fully disclosed hereinafter.

BRIEF DESCRIPTION OF THE INVENTION

The body oils of the present invention contain all-natural ingredients, such as a base oil of virgin olive oil alone or with canola oil; flavorants/fragrances such as cinnamon, peppermint, spearmint, or cloves; sensory materials such as menthol or cayenne pepper; colorizers such as paprika; sweeteners such as honey; and secondary flavorants such as cherry, strawberry, chocolate and the like. Such body oils provide pleasant aromas, sensory stimulation when applied, and are safely ingestible by an average user in reasonable amounts.

Therefore, it is an object of the present invention to provide body oils that are not harmful if ingested.

It is a further object to provide body oils that, if ingested, have a pleasant taste.

It is a further object to provide body oils that provide sensory stimulation to the skin after the body oil has been applied.

DETAILED DESCRIPTION AND PRESENTLY PREFERRED EMBODIMENTS

The body oils of the present invention contain all-natural ingredients. Preferably a base oil, such as virgin olive oil, which serves as a carrier for flavoring(s) or fragrance(s), sensory material(s), and optionally a sweetener. The base oil is present in a major proportion in relation to the other materials. The virgin olive oil can be combined with canola oil to enhance the sweetness of the final product.

Preferred flavorings and/or fragrances include peppermint leaves, spearmint leaves, peppermint oils, spearmint oils, cloves or clove oils, cinnamon, and cinnamon/canola oil flavorings. The peppermint or spearmint leaves will be crushed prior to use. Canola oil is preferably present when cinnamon and/or peppermint oils are used to enhance their flavors. These flavorings and/or fragrances can also be combined with secondary flavorants such as cherry, strawberry, chocolate or the like. For example, chocolate used in combination with the peppermint leaves or oils provides a pleasant chocolate mint flavor.

Preferred sensory materials provide stimulation to the skin, in addition to the sensations provided by the flavorings and/or fragrances, and can be menthol, menthol crystals, or cayenne pepper. The cayenne pepper will have a heat unit which is sufficient to provide sensory stimulation, for example from about 15,000 to 90,000 heat units, preferably about 90,000 heat units. One preferred embodiment combines the use of peppermint with cayenne pepper to provide for both a hot and cold sensory effect.

Paprika or other natural material(s) can be provided to add color to the body oils when desired. A sweetener, such as honey, can also be optionally present to enhance the taste of the body oils. Also, as mentioned above, canola oil in a lesser amount as compared to the base olive oil can be used to enhance the sweetness, and thus the flavor, of the body oil end product.

Such body oils are useful for those desiring all-natural oils or moisturizers, for use in massage or aroma therapy, for use as a sexual stimulant or "erotic" body oil, and as a muscle relaxant.

Without intending to limit the scope of the present invention, products and methods of production of the present invention can be better understood by referring to the examples set forth below.

EXAMPLE 1

A cinnamon body oil was prepared as follows. Two gallons of pure water were combined with two pounds of whole cinnamon sticks. The combination was boiled for approximately two hours, the water drained and added to approximately 6 liters of extra virgin olive oil and simmered until all of the water had evaporated. One pound of 90,000 heat unit cayenne pepper and half a pound of paprika were added to the oil and simmered for one hour. The oil was then filtered through a 5 micron filter paper. A cinnamon/canola oil flavor was then added and simmered for 15 minutes. The resulting oil was then cooled and bottled.

EXAMPLE 2

A spearmint or peppermint body oil was prepared as follows. One pound of crushed peppermint or spearmint leaves were added to 3 liters of virgin olive oil and heated to a slow simmer for one hour. The oil was then filtered through a 5 micron filter paper. For a peppermint oil end product, one ounce of menthol was added and allowed to simmer for 15 minutes. For a spearmint oil end product, one half ounce of menthol was added and allowed to simmer for 15 minutes. The resulting oil was then cooled and bottled.

EXAMPLE 3

A clove body oil was prepared as follows. Two gallons of pure water were combined with two pounds of cloves. The combination was boiled for approximately two hours and the remaining liquid drained off. The drained liquid was then added to approximately 3 liters of extra virgin olive oil and simmered until all of the water had evaporated. The oil was then filtered through a 5 micron filter paper. One half ounce of menthol was then added and simmered for 15 minutes. The resulting oil was then cooled and bottled.

A preferred body oil composition based on a combination of flavorants and fragrances includes peppermint, cloves, cherries, cinnamon, olive oil base oil in combination with canola oil, honey, ginger, cayenne pepper, paprika, spearmint and menthol. This combination provides both a hot and cold sensory effect while providing a complementary sweet flavor. The method of preparation follows the general lines of preparation used in the preparation of the cinnamon and peppermint oils as described above.

Although a few exemplary embodiments of the present invention have been described in detail above, those skilled in the art readily appreciate that modifications are possible without materially departing from the novel teachings and advantages which are described herein. Accordingly, all such modifications are intended to be included within the scope of the present invention, as defined by the following claims.

It is claimed:

1. A method of providing a sensory stimulating safely ingestible body oil comprising the steps:
   combining water with a quantity of cinnamon sticks to form a combination;
   boiling the combination;
   draining the water remaining following boiling from the combination and adding the water drained to virgin olive oil to form a mixture;
   simmering the mixture until substantially all the water evaporates leaving a flavored oil;
   adding cayenne pepper to the flavored oil;
   adding paprika to the flavored oil;
   filtering the flavored oil; and
   cooling the flavored oil.

2. A method according to claim 1 wherein said water combined with the cinnamon sticks is in an amount of about one gallon of water per each approximate pound of cinnamon sticks.

3. A method according to claim 1 wherein the combination is boiled for approximately two hours.

4. A method according to claim 1 wherein the virgin olive oil is provided in an amount of about six liters of virgin olive oil per each approximate two gallons of water.

5. A method according to claim 1 wherein the cayenne pepper provides a hot sensory stimulation to a human body and is added to the flavored oil in an amount of about one pound of cayenne pepper per every approximate two pounds of cinnamon sticks.

6. A method according to claim 1 wherein the paprika is added to the flavored oil in an amount of about one half pound of paprika per every approximate two pounds of cinnamon sticks.

7. A method according to claim 1 further comprising the addition of a secondary flavorant to the flavored oil.

8. A method of providing a sensory stimulating safely ingestible body oil comprising the steps:
   combining virgin olive oil with crushed peppermint leaves or crushed spearmint leaves to form a combination;
   heating the combination;
   filtering the combination through a filter;
   adding menthol to the combination and allowing the combination to simmer; and
   cooling the combination now present as a body oil.

9. A method according to claim 8 wherein the virgin olive oil is provided in an amount of about 3 liters of olive oil per each approximate pound of crushed peppermint leaves or crushed spearmint leaves.

10. A method according to claim 8 wherein the combination is heated to a simmer for about one hour.

11. A method according to claim 8 wherein when crushed peppermint leaves are added, the menthol is added in an amount of about one ounce per approximate pound of crushed peppermint leaves.

12. A method according to claim 8 wherein when crushed spearmint leaves are added, the menthol is added in an amount of about one half ounce per approximate pound of crushed spearmint leaves.

13. A method according to claim 8 further comprising adding a secondary flavorant to the combination.

14. A method of providing a sensory stimulating safely ingestible body oil comprising the steps:
   combining water with a quantity of cloves to form a combination;
   boiling the combination;
   draining the water remaining following boiling from the combination and adding the water drained to virgin olive oil to form a mixture;
   simmering the mixture until substantially all the water in the mixture evaporates leaving a flavored oil;
   adding menthol to the flavored oil;
   filtering the flavored oil; and
   cooling the flavored oil.

15. A method according to claim 14 wherein the cloves are combined with the water in an amount of about one gallon of water per each approximate pound of cloves.

16. A method according to claim 14 wherein the combination of water and cloves is boiled for approximately two hours.

17. A method according to claim 14 wherein the virgin olive oil is provided in the mixture in an amount of about three liters of virgin olive oil per each approximate two gallons of water.

18. A method according to claim 14 wherein the menthol is added to the flavored oil in an amount of about one half ounce per every approximate two pounds of cloves.

19. A method according to claim 14 further comprising adding a secondary flavorant to the flavored oil.

20. A sensory stimulating safely ingestible body oil produced by the method of any of claims 1, 2, 3, 4, 5, 6 or 7.

21. A sensory stimulating safely ingestible body oil produced by the method of any of claims 8, 9, 10, 11, 12 or 13.

22. A sensory stimulating safely ingestible body oil produced by the method of any of claims 14, 15, 16, 17, 18 or 19.

23. A body oil consisting essentially of a natural ingestible carrier oil, at least one natural ingestible flavor or fragrance material, at least one natural ingestible sensory material and, optionally, at least one natural ingestible sweetener, wherein such are present in amounts sufficient to provide a sensory stimulating safely ingestible body oil.

24. A body oil comprising a combination of cinnamon sticks, virgin olive oil, cayenne pepper and paprika, wherein such are present in amounts sufficient to provide a sensory stimulating safely ingestible body oil.

25. A body oil comprising a combination of crushed peppermint leaves or crushed spearmint leaves, virgin olive oil and menthol, wherein such are present in amounts sufficient to provide a sensory stimulating safely ingestible body oil.

26. A body oil comprising cloves, virgin olive oil and menthol, wherein such are present in amounts sufficient to provide a sensory stimulating safely ingestible body oil.

27. A body oil according to any of claims 24, 25 or 26 further comprising a natural ingestible sweetener.

28. A body oil according to any of claims 24, 25 or 26 further comprising a secondary flavorant.

* * * * *